United States Patent
Khavinson

(10) Patent No.: US 6,727,227 B1
(45) Date of Patent: Apr. 27, 2004

(54) TETRAPETIDE REVEALING GEROPROTECTIVE EFFECT, PHARMACOLOGICAL SUBSTANCE ON ITS BASIS, AND THE METHOD OF ITS APPLICATION

(75) Inventor: Vladimir K. Khavinson, St. Petersburg (RU)

(73) Assignee: Obschestvo S Ogranichennoi Otvetstven-Nostiju "Klinika Instituta Bioregulyatsii Gerontologii", St. Petersburg (RU)

( * ) Notice: Subject to any disclaimer, the term of this patent is extended or adjusted under 35 U.S.C. 154(b) by 0 days.

(21) Appl. No.: 09/959,852
(22) PCT Filed: Jan. 20, 2000
(86) PCT No.: PCT/RU00/00012
§ 371 (c)(1), (2), (4) Date: Mar. 6, 2002
(87) PCT Pub. No.: WO00/68255
PCT Pub. Date: Nov. 16, 2000

(51) Int. Cl.[7] .......................... A61K 38/07; C07K 5/10
(52) U.S. Cl. ........................................ 514/18; 530/330
(58) Field of Search .............................. 514/18; 530/330

(56) References Cited

PUBLICATIONS

Khavison et al. The neurite–stimulating effect of peptides from brain in dorsal root ganglion neuron organotypic culture. Prim. Sensory Neuron. 1997, vol. 2, No. 3, pp. 191–200.*
Anisimov et al. Effect of melatonin and pineal peptide preparation epithalamin on life span . . . Mechanisms of Ageing and Development. 1997, vol. 97, pp. 81–91 (abstract only).*
Abstract of Japanese Patent Application 8–051980 (Feb. 27, 1996).*
Geokas et al. The Aging Process. Annals Int. Med. Sep. 15, 1990, vol. 113, No. 6, pp. 455–466.*
Schneider et al. Life Extension. N. Eng. J. Med. May 2, 1985, vol. 312, No. 18, pp. 1159–1168.
L. Hayflick. Theories Of Biological Aging. Experimental Gerontology. 1985, vol. 20, pp. 145–159.
Templeton et al. The Proximate And Ultimate Control Of Aging In Drosophila And Humans. Basic Life Sci. 1987, vol. 42, pp. 123–133.

* cited by examiner

Primary Examiner—Jeffrey E. Russel
(74) Attorney, Agent, or Firm—Whitham, Curtis & Christofferson, P.C.

(57) ABSTRACT

Tetrapeptide L-alanyl-L-glutamyl-L-aspartyl-glycine (SEQ ID NO: 1) of the general formula L-Ala-L-Glu-L-Asp-Gly (SEQ ID NO: 1) is proposed as a biologically active compound with a geroprotective effect. The use of L-Ala-L-Glu-L-Asp-Gly (SEQ ID NO: 1) tetrapeptide in medicine is proposed for preparing a substance displaying a geroprotective effect. There is proposed a pharmacological substance, which contains as its active base an effective amount of tetrapeptide of the formula L-alanyl-L-glutamyl-L-aspartyl-glycine (L-Ala-L-Glu-L-Asp-Gly) (SEQ ID NO: 1) or its salts of the amino group (acetate, hydrochloride, oxalate) and of carboxyl groups (the salts of metals-Sodium, Potassium, Calcium, Lithium, Zinc, Magnesium, and also the salts of organic and inorganic cations-ammonium and triethylammonium). The substance is proposed for parenteral, intranasal, oral administration, and local application. With respect to the invention, the method of premature ageing prevention involves prophylactic and/or therapeutic administration to a patient of the pharmacological substance in doses of 0.01 to 100 μg/kg of the body weight at least once a day for a period necessary for the achievement of a therapeutic effect.

20 Claims, No Drawings

TETRAPEPTIDE REVEALING GEROPROTECTIVE EFFECT, PHARMACOLOGICAL SUBSTANCE ON ITS BASIS, AND THE METHOD OF ITS APPLICATION

FIELD OF INVENTION

The invention relates to the field of medicine and may be employed as a geroprotective substance for the prevention of premature ageing of the organism.

It is known that some of the main mechanisms of the organism ageing are: an increase in molecular lesions caused by free radicals, functional disturbances of the anti-oxidation defence system, and disorder in physiological functions of the epiphysis (1, 2, 3).

BACKGROUND OF THE INVENTION

Since the claimed tetrapeptide, according to the invention, displays biological activity, and namely, geroprotective activity, a group of compounds possessing anti-oxidation properties must be referred to as analogues in application. Ionol food-supplement (2.6-di-tert-butyl4-methylphenol), being a well-known inhibitor of radical processes, has promoted an increase in the life span of $LAF_1$ strain in mice characterised by accelerated ageing (4). However, the pharmaceutical based on 2.6-di-tert-butyl-4-methylphenol (dibunol) is manufactured in the form of a liniment and is largely applied in urology practice for treatment of cancer patients (5). Addition of ethoxyhin anti-oxidant (santohin) to food extended the life span of mice of C3H strain (6). An increase in the life span of experimental animals is also promoted by 2-ethyl-6-methyl-3-oxypyridine chlorhydrate, a low-toxic water-soluble anti-oxidant, which is a structural analogue of vitamin $B_6$ (7, 8). An insignificant extension in the life span of experimental animals was facilitated by 2-mercaptoethanolamine, butyl hydroxytoluol, cystein, 3-hydroxypyridine, centrophenoxyn, lactic and gluconic acids, and glutathione (9, 10). Still, these compounds are not pharmaceutical preparations and they have found no employment in medicine as geroprotective substances. Administration of vitamins A, C, E resulted in an increase in the life span of experimental animals as well (11, 12, 13). Supersaturation of the organism with these vitamins, however, can unfavourably influence the functions of organs and systems and entail an intensive development of hypervitaminosis. β-catechol, a preparation whose composition is formed by vitamins and vegetable substances, is known to display anti-oxidation activity (14). Administration of this preparation to SAM-P8 strain mice showing accelerated ageing augmented the survival rate of the animals. However, the mechanisms of its geroprotective action have not been studied enough yet, thus limiting its integration with clinical practice. After the mice of SAM strain, disposed to accelerated ageing, had been kept on a diet with an increased amount of carnosine (β-Ala-His) for 7 months, their death rat decreased (15).

Still, carnosine is not a pharmaceutical preparation, its geroprotective properties being not studied enough yet. A minor increase in the average life span of mice was affected by the application of melatonin, an epiphyseal hormone (16). The impact of melatonin is associated with its anti-oxidation property (17). Nevertheless, the melatonin exposure of Drosophila melanogaster selected for a high embryonic mortality rate (HEM strain), failed to produce a geroprotective effect, though it was accompanied by an anti-oxidation one. Melatonin is not a pharmaceutical preparation and is manufactured in the form of a biologically active food additive.

Gerovital, a Novocain-containing drug, is used as a geroprotective substance. The detriments of this preparation consist in its possible negative influence on the functions of the cardiovascular system, its allergic impact, sometimes sleep impairment, feeling of anxiety, muscular and articular pains.

DISCLOSURE OF THE INVENTION

The claimed invention is aimed at obtaining a new biologically active compound of peptide origin capable of geroprotective activity.

The claimed peptide compound—tetrapeptide—has no structural analogues.

According to the invention, there is claimed tetrapeptide L-alanyl-L-glutamyl-L-aspartyl-glycine of the general formula L-Ala-L-Glu-L-Asp-Gly (SEQ ID NO: 1).

With respect to the invention, the tetrapeptide L-alanyl-L-glutamyl-L-aspartyl-glycine with the following amino acid sequence: L-Ala-L-Glu-L-Asp-Gly (SEQ ID NO: 1) reveals biological activity, namely, geroprotective activity due to the stimulation of indices of the anti-oxidation defence system and due to the process of melatonin synthesis in structures of the diffuse neuroendocrine system.

The tetrapeptide is obtained by a classical method of peptide synthesis in a solution (19).

The geroprotective activity of L-Ala-L-Glu-L-Asp-Gly tetrapeptide (SEQ ID NO: 1) was stated in experimental trials. The study of geroprotective activity was conducted in Drosophila melanogaster by analysing the indices of anti-oxidation defence, life span, and the length of reproduction period, as well as in rats by examining the synthesis of extra-pineal melatonin.

With respect to the invention, the pharmacological substance capable of geroprotective activity includes as its active base an effective amount of tetrapeptide of the formula L-alanyl-L-glutamyl-L-aspartyl-glycine (L-Ala-L-Glu-L-Asp-Gly) (SEQ ID NO: 1) or its salts.

With respect to the invention, the pharmacological substance capable of geroprotective activity may contain salts of the amino group (acetate, hydrochloride, and oxalate) or of carboxyl groups (the salts of metals—Sodium, Potassium, Calcium, Lithium, Zinc, Magnesium, and other organic and inorganic cations—ammonium, triethylammonium).

With respect to the invention, the pharmacological substance is meant for parenteral, intranasal, oral administration, or local application.

The claimed pharmacological substance displaying geroprotective activity is capable of stimulating the indices of the anti-oxidation defence system and the processes of melatonin synthesis in structures of the diffuse neuroendocrine system, which, in their turn, inhibit ageing processes and promote a life span increase.

The notion "geroprotective substance", used in this application, implies the substance, which inhibits ageing and prolongs life by means of preventing premature ageing, which needs stimulation of the anti-oxidation defence system and the regulatory influence on metabolic processes in structures of the diffuse neuroendocrine system.

The notion "pharmacological substance", used in this application, implies the employment of any drug form containing the tetrapeptide or its salts, which can be used for prophylactic and/or therapeutic purposes in medicine as a geroprotective substance in premature ageing.

The notion "effective amount", used in this application, implies the employment of such an amount of the active base, which, in compliance with its quantitative indices of activity and toxicity, as well as with respect to the knowledge available, must be effective in this drug form.

The notion "pharmaceutical composition", used in this application, implies various drug forms of the preparation.

In order to obtain pharmaceutical compositions, in accordance with the invention, the proposed tetrapeptide or its pharmaceutically applicable derivatives are mixed as an active ingredient and a pharmaceutical carrier in accordance with the methods of compounding accepted in pharmaceutics.

The carrier can have various forms, which depend on the drug form of the preparation desirable for administration, for example: parenteral, intranasal, or oral.

All known pharmacological components can be used for the preparation of compositions in doses preferable for oral administration.

For parenteral (intranasal) administration, the carrier usually includes sterile water, although there can be included other ingredients instrumental for stability or maintaining sterility.

In accordance with the invention, the method embraces the prophylactic or therapeutic exposure of patients to the claimed pharmacological substance in doses of 0.01 to 100 μg/kg of the body weight, at least once a day during a period necessary for achieving a therapeutic effect—10 to 40 days depending on the character and severity of a pathologic process.

In accordance with the invention, the tetrapeptide is active when administered in doses of 0.01 to 100 μg/kg of the body weight, although lower (higher) doses can be used as well, depending on the character and severity of a pathologic process.

INDUSTRIAL APPLICATION

The invention is illustrated by an example of synthesis of the tetrapeptide, whose formula is L-alanyl-L-glutamyl-L-aspartyl-glycine (L-Ala-L-Glu-L-Asp-Gly) (SEQ ID NO: 1) (Example 1), by the examples of tests for toxicity and biological activity of the tetrapeptide (Examples 2–8), and also by examples which show the results of clinical application of the tetrapeptide, thus demonstrating its pharmacological properties and attesting the possibility of achieving a prophylactic and/or therapeutic effect (Examples 9, 10).

EXAMPLE 1

Synthesis of L-Ala-L-Glu-L-Asp-Gly Tetrapeptide (SEQ ID NO: 1)

1. Product name: L-alanyl-L-glutamyl-L-aspartyl-glycine (SEQ ID NO: 1)

2. Structural formula: H-Ala-Glu-Asp-Gly-OH (SEQ ID NO: 1).

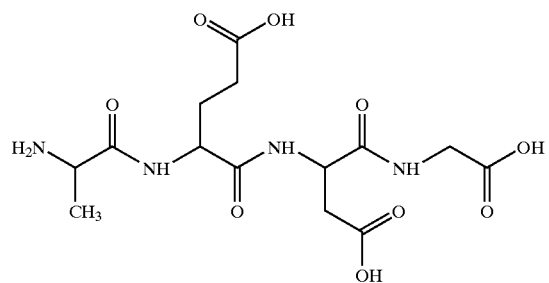

3. Molecular formula without ion pair: $C_{14}H_{22}N_4O_9$.
4. Molecular weight without ion pair: 390.35.
5. Ion pair: acetate.
6. Appearance: white amorphous powder without smell.
7. Method of synthesis: the peptide is obtained by a classical method of synthesis in a solution by the following scheme:

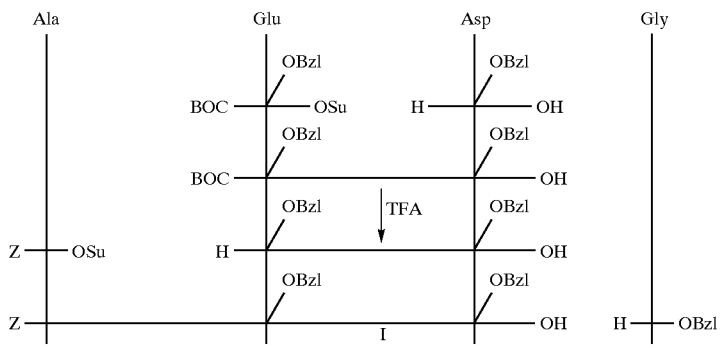

Z—benzyloxycarbonyl group
BOC—tert.butyloxycarbonyl group
OSu—N-oxysuccinimide ester
OBzl—benzyl ester
DCC—N, N'-dicyclohexylcarbodiimide
HOBT—N-oxybenzotriazol N, N'-dimethylformamide was used as a solvent. By the addition of aspartic acid the α-COOH group was protected by the salification method with the use of triethylamine. The removal of the BOC-protecting group was performed with a solution of trifluoracetic acid (TFA); the removal of the Z-protecting group was performed with catalytic hydrogenation. The extraction and purification of the product were conducted by the method of preparative high-performance liquid chromatography (HPLC) on the column with a reversed phase.

Properties of the final product:

| amino acid analysis | | | |
|---|---|---|---|
| Glu | Asp | Ala | Gly |
| 1.02 | 1.00 | 1.01 | 1.00 | peptide content: 98.4% (by HPLC, 220 nm)
thin layer chromatography (TLC)-individual, $R_f$=0.73 (acetonitrile-acetic acid-water, 5:1:3)

moisture content: 5% pH of the 0.001%-solution: 4.37 specific rotary power: $[\alpha]_D^{22}$: −32° (c=1, $H_2O$)

Example of Synthesis

1. BOC-Glu(OBzl)-Asp(OBzl)-OH(I), N-tert.butyloxycarbonyl-(γ-benzyl)glutamyl-(β-benzyl)aspartate 4.3 g (0.0100 mole) of N-oxysuccinimide ester of N-tert.butyloxycarbonyl-(γ-benzyl) glutamic acid (BOC-Glu(OBzl)-OSu) are dissolved in 20 ml of dimethylformamide and added 1.72 ml (0.0125 mole) of triethylamine and 2.80 g (0.0125 mole) of β-benzylaspartate. The mixture is stirred for 24 hours at room temperature. Afterwards the product is precipitated with 0.5 N (150 ml) of sulphuric acid, extracted by ethyl acetate (3×33 ml), washed in 0.5 N of sulphuric acid (2×20 ml), water, 5%-solution of sodium bicarbonate (1×20 ml), water, 0.5 N of sulphuric acid (2×20 ml), water, the solution is dried over anhydrous $Na_2SO_4$. Ethyl acetate is filtered out and removed in vacuo under 40° C. The residue is dried in vacuo over $P_2O_5$. As a result, 5.68 g (≈100%) of oil is obtained. $R_f$=0.42 (benzene-acetone 2:1, Sorbfil plates, 8–12 μm Silicagel, UV and chlorine/benzidine development).

2. TFA H-Glu(OBzl)-Asp(OBzl)-OH(II), (γ-benzyl)glutamyl-(β-benzyl)aspartate trifluoracetate 5.68 g (≈0.01 mole) of N-tert.butyloxycarbonyl-(γ-benzyl)glutamyl-(β-benzyl)aspartate (I) are dissolved in 20 ml of dichloromethane-trifluoracetic acid mixture (3:1). In 2 hours the solvent is removed at 40° C. The removal is repeated with an addition of another portion of dichloromethane (2×10 ml), the residue is dried in vacuo over NaOH. 5.80 g (≈100%) of oil are obtained. $R_f$=0.63 (n-butanol-pyridine-acetic acid-water, 15:10:3:12).

3. Z-Ala-Glu(OBzl)-Asp(OBzl)-OH(III), N-carbobenzoxyalanyl-(γ-benzyl)glutamyl-(β-benzyl)aspartate 5.65 g (0.01 mole) of (γ-benzyl)glutamyl-(β-benzyl)aspartate trifluoracetate (II) are dissolved in 10 ml of dimethylformamide, added with 2.80 ml (0.02 mole) of triethylamine and 4.14 g (0.013 mole) of N-oxysuccinimide ester of N-carbobenzoxyalanyl. The reacting mixture is stirred at room temperature for 24 hours. The product is precipitated with 0.5 N of sulphuric acid (150 ml), extracted by ethyl acetate (3×30 ml), washed in 0.5 N of sulphuric acid (2×20 ml), water, 5%-solution of sodium bicarbonate (1×20 ml), water, 0.5 N of sulphuric acid (2×20 ml), water. The solution is dried over anhydrous $Na_2SO_4$. Ethyl acetate is filtered out, removed in vacuo at 40° C. The residue is recrystallised in the ethyl acetate/hexane system. The product is filtered and dried in vacuo over $P_2O_5$. The yield is 4.10 g (66%). The melting point ($T_{ml}$) is 154° C. $R_f$=0.48 (benzene-acetone, 1:1), $R_f$=0.72 (n-butanol-pyridine-acetic acid-water, 15:10:3:12).

4. Z-Ala-Glu(OBzl)-Asp(OBzl)-Gly-OBzl(IV), N-carbobenzoxyalanyl (γ-benzyl)glutamyl-(β-benzyl)aspartylglycine benzyl ester 1.01 g (3 mmole) of benzyl ester of glycine tosilate TosOH H-Gly-OBzl is suspended in 15 ml of tetrahydrofuran and added with 0.4 ml (3 mmole) of triethylamine while mixing, then, in 5 minutes, is added with 1.28 g (2 mmole) of N-carbobenzoxyalanyl-(γbenzyl) glutamyl-(β-benzyl)aspartate(III) and 0.27 g (2 mmole) of N-oxybenzotriazol. The mixture is cooled down to 0° C. Afterwards, there are added 0.42 g (2 mmole) of N,N'-dicyclohexylcarbodiimide solution in 5 ml of tetrahydrofuran cooled down to 0° C. The mixture is stirred at this temperature for 2 hours and left for a night at room temperature. The residue of dicyclohexylurea is filtered out, the solvent is removed in vacuo and the residue is dissolved in 30 ml of ethyl acetate. The solution is washed in 1 N of sulphuric acid, water, 5% solution of sodium bicarbonate, water, 1 N of sulphuric acid, water, and dried over anhydrous $Na_2SO_4$. The solvent is removed in vacuo and the product is recrystallised in the ethyl acetate/hexane system. The yield is 1.30 g (82%). $T_{ml}$=146–148° C. $R_f$=0.75 (benzene-acetone, 2:1).

5. H-Ala-Glu-Asp-Gly-OH(V), alanyl-glutamyl-aspartyl-glycine (SEQ ID NO: 1)

1.25 g of N-carbobenzoxyalanyl-(γ-benzyl)glutamyl(β-benzyl)aspartylglycine benzyl ester (III) are hydrogenated in the methanol-water-acetic acid system (3:1:1) over Pd/C. Progress of the reaction is monitored by TLC in benzene-acetone (2:1) and acetonitrile-acetic acid-water (5:1:3) systems. After the end of the reaction the catalyst is filtered, the filtrate is removed in vacuo, and the residue is recrystallised in a water-methanol system. The product is dried in vacuo over KOH. The yield is 520 mg (95%). $R_f$=0.73 (acetonitrile-acetic acid-water, 5:1:3). For purification, 390 mg of the product is dissolved in 4 ml of 0.01% triflouracetic acid and subjected to HPLC on the column with a reversed phase 50×250 mm Diasorb-130-C16T, 7 μm. The chromatograph used is Beckman System Gold, 126 Solvent Module, 168 Diode Array Detector Module. The conditions of chromatography A: 0.1% TFA; B: 50% MeCN/0.1% TFA, gradient B 0→5% during 80 min. Sample volume constitutes 5 ml, detection is conducted at 215 nm, scanning-from 190–600 nm, the flow speed is 10 ml/min. The fraction is collected within 54.0–66.0 min. The solvent is removed in vacuo at a temperature not exceeding 40° C., it is multiply repeated (5 times) with 10 ml of 10% solution of acetic acid. Finally the residue is dissolved in 20 ml of deionised water and lyophilised. As a result there is obtained 290 mg of purified product in the form of an amorphous white powder without smell. The obtained peptide in the form of acetate is transferred to a free form by processing it with IRA anionite or with an analogous substance in the (OH)-form. Afterwards, salts of the amino group are obtained with the subsequent addition of an equivalent of a corresponding acid (hydrochloride or oxalic). The obtained water solution is lyophilised and analysed as a final product.

In order to obtain corresponding salts of carboxyl groups, the free tetrapeptide is added with a calculated amount of the water solution of hydroxide of a corresponding metal (NaOH, KOH, $Zn(OH)_2$, LiOH, $Ca(OH)_2$, $Mg(OH)_2$, $NH_4OH$). To obtain triethylammonium salt, the processing is carried out similarly, with the use of triethylamine as a base.

6. Analysis of the final product

Peptide content is determined by HPLC on the Surelco LC-18-DB column, 4.6×250 mm, grad. LC-18-DB. A: 0.1% of TFA; B: 50% of MeCN/0.1% of TFA; grad. B 0→20% during 30 min. The flow speed is 1 ml/min. Detection at 220 nm, scanning—from 190–600 nm, the sample volume is 20 μl. Peptide content—98.45%.

The amino acid analysis is carried out on the tester AAA "T-339" Prague. Hydrolysis is conducted in 6 N of HCl at 125° C. for 24 hours

| Glu | Asp | Ala | Gly |
|---|---|---|---|
| 1.02 | 1.00 | 1.01 | 1.00 |

TLC: individual, $R_f$=0.73 (acetonitrile-acetic acid-water, 5:1:3). Sorbfil plates, 8–12 μm Silicagel, development in chlorine/benzidine.

Moisture content: 5% (gravimetrically according to the mass loss by drying, −20 mg at 100° C.).

pH of 0.001% solution: 4.37 (potentiometrically).

Specific rotary power: $[\alpha]_D^{22}$: −32° (c=1, H$_2$O), "Polamat A", Carl Zeiβ Jena.

EXAMPLE 2

Study of L-Ala-L-Glu-L-Asp-Gly Tetrapeptide (SEQ ID NO: 1) for Toxicity

The study of L-Ala-L-Glu-L-Asp-Gly tetrapeptide (SEQ ID NO: 1) for general toxicity was conducted in accordance with "The rules of pre-clinical estimation of the safety of pharmacological substances" (GLP).

The purpose of the study was to define tolerable toxic doses of the preparation, to estimate the stage and character of pathologic alterations in various organs and systems of the organism, and to identify the correlation between the toxic dose-related effect and the duration of the drug application.

Determination of acute toxicity of L-Ala-L-Glu-L-Asp-Gly tetrapeptide (SEQ ID NO: 1) was conducted according to Kerber. The investigation was carried out on 66 white outbred male mice weighing 20 to 23 g, which were kept under standard regimen and fed upon standard rations in vivarium conditions. The animals were randomly divided into 6 equal groups of 11 mice in each. The animals were exposed to a single administration of the drug intramuscularly, 0.25 ml in doses 1 mg/kg, 2 mg/kg, 3 mg/kg, 4 mg/kg and 5 mg/kg (several thousand times exceeding the therapeutic dose recommended for clinical trial). Control animals were administered the same amount of sodium chloride.

Within 72 hours and later on in 14 days none of the animals in either of the groups died. No alterations in the general state, behaviour, locomotor activity, hair and skin integument, or physiological discharges of the animals were registered.

Thus, L-Ala-L-Glu-L-Asp-Gly tetrapeptide (SEQ ID NO: 1) in doses several thousand times exceeding the therapeutic one, recommended for clinical trials, does not induce acute toxic reactions, which confirms a wide therapeutic applicability of the preparation.

The study of subacute toxicity of L-Ala-L-Glu-L-Asp-Gly tetrapeptide (SEQ ID NO: 1) was carried out on 60 white outbred rats with body weight 150 to 250 g. Experimental animals were exposed daily to a single administration of the drug intramuscularly for 90 days in doses 1 μg/kg, 0.3 mg/kg, 3 mg/kg in 0.5 ml of sodium chloride solution. Animals of the control group were administered with the same amount of sodium chloride.

Within the whole period of study the animals were under daily observation. Behaviour of the animals, their rations and water consumption, the state of hair integument and mucous membranes were registered. The animals were weighed weekly. Prior to and on the $30^{th}$, $60^{th}$, and $90^{th}$ days of the drug administration the morphological composition and properties of the peripheral blood were examined. Upon the experiment completion biochemical and coagulologic indices of blood were investigated.

Chronic toxicity of L-Ala-L-Glu-L-Asp-Gly tetrapeptide (SEQ ID NO: 1), obtained by the claimed method, was studied by its long-time administration to rats with body weight 150 to 250 g. The animals were exposed daily to a single administration of the drug intramuscularly in doses 1 μg/kg, 0.1 mg/kg, 1 mg/kg in 0.5 ml of sodium chloride solution during 6 months. Behaviour of the animals, their rations and water consumption, the state of their hair integument and mucous membranes were registered. The animals were weighed daily during the first 3 months of the experiment and then once a month. Haematological and biochemical studies were carried out 3 months after the onset of drug administration and upon experiment completion. Functions of the cardiovascular system, liver, pancreas, kidneys, and adrenal glands were assessed. Upon the end of drug administration some animals were subjected to pathomorphological examination for the purpose of estimating the condition of various sections of the brain and spinal marrow, heart, aorta, lungs, liver, kidneys, organs of the endocrine and immune systems.

Estimation of the general state of the animals, the morphological and biochemical indices of the peripheral blood, the morphological state of the intrinsic organs, the state of the cardiovascular and respiratory systems, liver and kidney functions showed no pathologic alterations.

The study of subacute and chronic toxicity of L-Ala-L-Glu-L-Asp-Gly tetrapeptide (SEQ ID NO: 1) confirms the absence of side effects in case of long-term application of the drug in doses, which 100–1000 times exceeded the therapeutic one.

EXAMPLE 3

Impact of L-Ala-L-Glu-L-Asp-Gly tetrapeptide (SEQ ID NO: 1) on the Ageing Rate and Free Radical Processes in *Drosophila Melanogaster* of HEM Strain Selected for High Embryonic Mortality Rate L-Ala-L-Glu-L-Asp-Gly tetrapeptide (SEQ ID NO: 1) was applied in *Drosophila melanogaster* larvae of the $2^{nd}$ age of HEM strain selected for a high ageing rate (20). HEM strain is characterised by the unique dynamics of embryonic mortality, which consists in an increased frequency of early embryonic lethal outcomes from 65% on the $1^{st}$ day of egg-laying up to 95% on the $4^{th}$ day, in a reduced average life span (29 days), and in a raised intensity of lipid peroxide oxidation.

L-Ala-L-Glu-L-Asp-Gly tetrapeptide (SEQ ID NO: 1) was added in proportion 0.00001% of the culture medium weight, which was an extremely low dose. The doses described in literature on the influence of various substances on *Drosophila melanogaster* usually ranged from 0.001 to 0.01%. Lower doses do not normally produce any effect.

Biochemical parameters were studied on 14-day old flies. Among them the activity of catalase activity and the intensity of tissue chemoluminescence were analysed (21, 22, 23). Catalase is the basic enzyme of anti-oxidation defence. The degree of its activity suggests the ability of the organism to withstand oxidative stress. Luminol-dependent chemoluminescence, induced by hydrogen peroxide, reflects the stage of active oxygen forms in tissues. Thus, a decrease in the chemoluminescence intensity indicates an increase in the organism ability to resist oxidative stress.

The obtained results are displayed in Table 1. Since significant intersexual distinctions on the studied indices have been revealed the data for females and males are given separately.

The presented data provide evidence that L-Ala-L-Glu-L-Asp-Gly tetrapeptide (SEQ ID NO: 1) promotes a significant rise in catalase activity in experimental male and female flies in comparison with the controls.

General anti-oxidation activity of tissues, characterised by the degree of chemoluminescence, increased under the influence of L-Ala-L-Glu-L-Asp-Gly tetrapeptide (SEQ ID NO: 1) only in females.

TABLE 1

Influence of L-Ala-L-Glu-L-Asp-Gly tetrapeptide (SEQ ID NO. 1) on catalase activity and tissue chemoluminescence in *Drosophila melanogaster* of HEM strain

| Variant of the experiment | Catalase activity (mmole $H_2O_2$/mg of protein per min.) | Chemoluminescence (conv. unit/ mg of protein) |
|---|---|---|
| FEMALES | | |
| Control | 85.5 ± 2.78 | 14.7 ± 1.44 |
| L-Ala-L-Glu-L-Asp-Gly Tetrapeptide (SEQ ID NO: 1) | 98.8 ± 1.62* | 7.9 ± 0.91* |
| MALES | | |
| Control | 115.4 ± 9.88 | 1.59 ± 0.121 |
| L-Ala-L-Glu-L-Asp-Gly Tetrapeptide (SEQ ID NO: 1) | 132.3 ± 3.68* | 2.03 ± 0.182 |

*$P < 0.05$ in comparison with the control indices.
Table 2 displays the results of the life span analysis in different experimental groups.

Table 2 displays the results of the life span analysis in different experimental groups.

TABLE 2

Influence of L-Ala-L-Glu-L-Asp-Gly tetrapeptide (SEQ ID NO: 1) on the life span parameters in *Drosophila melanogaster* of HEM strain

| Variant of the experiment | ALS (days) | Me (days) | 90% (days) | R · $10^{-2}$ (days$^{-1}$) | MRDT |
|---|---|---|---|---|---|
| FEMALES | | | | | |
| Control | 38 + 1.6 | 43.5 | 67 | 6.7 + 0.11 | 3.4 |
| L-Ala-L-Glu-L-Asp-Gly Tetrapeptide (SEQ ID NO: 1) | 48 + 1.5** | 48.0 | 76 | 4.0 + 0.29** | 3.9 |
| MALES | | | | | |
| Control | 40 + 1.5 | 43.5 | 64 | 5.5 + 0.27 | 3.6 |
| L-Ala-L-Glu-L-Asp-Gly Tetrapeptide (SEQ ID NO: 1) | 42 + 1.3 | 38.0 | 62 | 4.5 + 0.37* | 3.8 |

Note:
ALS - average life span;
Me - median life span;
90% - the age, which 90% of the individuals reach;
R · $10^{-2}$ - the parameter of Gomperz equation;
MRDT - mortality-rate doubling time.
*$P < 0.05$ in comparison with the control indices;
**$P < 0.001$ in comparison with the control indices.

As it is demonstrated in Table 2, L-Ala-L-Glu-L-Asp-Gly tetrapeptide (SEQ ID NO: 1) produces a pronounced gero-protective effect. In females it significantly extends the average life span ($P<0.001$) and lowers the ageing rate (R) ($P<0.001$). In males it slightly decreases the ageing rate ($P<0.05$).

Thus, L-Ala-L-Glu-L-Asp-Gly tetrapeptide (SEQ ID NO: 1) increases the average life span by 26% and reduces the population real ageing rate, estimated by the quantity of Gomperz parameter, by 40%.

EXAMPLE 4

Influence of L-Ala-L-Glu-L-Asp-Gly Tetrapeptide (SEQ ID NO: 1) on the Reproductive Functions in *Drosophila Melanogaster* of HEM Strain, Selected for High Embryonic Mortality Rate Influence of L-Ala-L-Glu-L-Asp-Gly tetrapeptide (SEQ ID NO: 1) upon *Drosophila melanogaster* was tested at the stage of larvae of the $2^{nd}$–$3^{rd}$ age, by means of adding the preparation to culture medium in dose 0.00001% of the medium weight, which approximately made 0.015 mg/100 ml. The flies, hatched on the $1^{st}$ day, were placed into test tubes, 5 couples in each, and transferred to fresh medium every 3 to 6 days.

There have been considered the following factors:
The share of the test tubes (of their initial amount), which contained live females (in Table 3—the share of live cultures).
The share of the test tubes (of the number of live cultures), in which posterity was given (in Table 3—the share of fertile cultures).

In each experimental variant 75 parental couples were analysed. The distinctions between fertility indices were defined by means of Fischer exact criterion for 2×2-adjustment tables (24).

The results of the experiment are displayed in Table 3. For each experimental variant the shares of live and fertile cultures are presented. As it is shown in the Table, starting from the $19^{th}$ day the share of tetrapeptide-processed fertile cultures exceeds the analogous share for the control. It is demonstrated that the share of fertile culture in L-Ala-L-Glu-L-Asp-Gly tetrapeptide (SEQ ID NO: 1) variant was notably higher ($P<0.05$) than in controls at the age of 32 days.

The coefficients of lineal regression are presented in Table 4. As it is shown in the Table, the coefficients of the control regression line differ significantly from the experimental one. The "a"-coefficient (reflecting the slope of the straight line) in the control is 1.8 times higher than the regression coefficient of the experimental variant.

Thus, it is demonstrated that the share of fertile cultures in the control variant reduces twice faster in comparison with the L-Ala-L-Glu-L-Asp-Gly tetrapeptide (SEQ ID NO: 1) variant. Duration of the reproductive period amounted to 30 days for the cultures, not exposed to the tetrapeptide, and to 47 days for the cultures processed with the tetrapeptide. It is shown that L-Ala-L-Glu-L-Asp-Gly tetrapeptide (SEQ ID NO: 1) 1.5-fold extends the reproduction period.

The data obtained on the life span were analysed correspondingly. The data on the regression 5 analysis are displayed in Table 5.

As it follows from the Table, the share of live cultures (i.e. the cultures, in which live females are present) decreases on average 1.5 times faster than in controls. The calculated median life span (i.e. the age, by which 50% individuals die) and the one that is really attained (i.e. the maximal life span in different variants of the experiment) are displayed in Table 6.

As it is demonstrated in the Table, in addition to an increase in the median life span, in the variant processed with L-Ala-L-Glu-L-Asp-Gly tetrapeptide (SEQ ID NO: 1) a maximal record-breaking rise in the life span was attained (in the strains of *Drosophila melanogaster* with high ageing rate)—100 days.

TABLE 3

Influence of L-Ala-L-Glu-L-Asp-Gly tetrapeptide (SEQ ID NO: 1) on the dynamics of live and fertile cultures share in *Drosophila melanogaster* of HEM strain

| | Control | | L-Ala-L-Glu-L-Asp-Gly tetrapeptide (SEQ ID NO: 1) | |
|---|---|---|---|---|
| | Share of cultures | | | |
| Days | Live | Fertile | Live | Fertile |
| 0 | 100 − 0.8 | 100 − 0.8 | 100 − 0.8 | 100 + 0.8 |
| 6 | 100 − 0.8 | 100 − 0.8 | 100 − 0.8 | 100 + 0.8 |
| 10 | 100 − 0.8 | 86 ± 9.3 | 100 − 0.8 | 93 ± 6.9 |
| 13 | 100 − 0.8 | 79 ± 11.0 | 100 − 0.8 | 93 ± 6.9 |
| 19 | 100 − 0.8 | 50 ± 13.4 | 100 − 0.8 | 86 ± 9.4* |
| 23 | 100 − 0.8 | 29 ± 12.1 | 100 − 0.8 | 43 ± 13.2 |
| 27 | 93 ± 6.9 | 15 ± 10.0 | 93 ± 6.9 | 31 ± 12.9 |
| 32 | 93 ± 6.9 | 0 + 0.8 | 85 ± 10.0 | 36 ± 14.5** |
| 38 | 93 ± 6.9 | 0 + 0.8 | 85 ± 10.0 | 9 ± 8.7 |
| 44 | 71 ± 12.0 | 0 + 0.8 | 85 ± 10.0 | 9 ± 8.7 |
| 50 | 7 + 6.9 | 0 + 0.8 | 36 ± 12.8 | 9 ± 8.7 |
| 54 | 7 + 6.9 | 0 + 0.8 | 36 ± 12.8 | 0 + 0.9 |
| 60 | 7 + 6.9 | 0 + 0.8 | 29 ± 12.1 | 0 + 0.9 |
| 66 | 7 + 6.9 | 0 + 0.8 | 29 ± 12.1 | 0 + 0.9 |
| 69 | 7 + 6.9 | 0 + 0.8 | 21 ± 10.9 | 0 + 0.9 |
| 73 | 7 + 6.9 | 0 + 0.8 | 7 ± 6.9 | 0 + 0.9 |
| 76 | 0 + 0.8 | 0 + 0.8 | 7 ± 6.9 | 0 + 0.9 |
| 84 | 0 + 0.8 | 0 + 0.8 | 7 ± 6.9 | 0 + 0.9 |
| 87 | 0 + 0.8 | 0 + 0.8 | 7 ± 6.9 | 0 + 0.9 |
| 100 | 0 + 0.8 | 0 + 0.8 | 0 + 0.8 | 0 + 0.9 |

*$P < 0.06$ in comparison with the control indices;
**$P < 0.05$ in comparison with the control indices.

TABLE 4

Coefficients of lineal regression for the dependence of fertile culture share on age ($y = B + A_x$)

| Coefficients | Control | L-Ala-L-Glu-L-Asp-Gly tetrapeptide (SEQ ID NO: 1) |
|---|---|---|
| B | 133 ± 4.2 | 115 ± 11.4 |
| A | −4.4 ± 0.22 | −2.5 ± 0.37* |

*$P < 0.001$ in comparison with the control indices.

TABLE 5

Coefficients of lineal regression for the dependence of live culture shares on age ($y = B + A_x$)

| Coefficients | Control | L-Ala-L-Glu-L-Asp-Gly tetrapeptide (SEQ ID NO: 1) |
|---|---|---|
| B | 160 ± 22.8 | 137 ± 10.6 |
| A | −2.4 ± 0.43 | −1.6 ± 0.17* |

*$P < 0.001$ in comparison with the control indices.

TABLE 6

Parameters of the life span in different experimental variants (days)

| Indices | Control | L-Ala-L-Glu-L-Asp-Gly tetrapeptide (SEQ ID NO: 1) |
|---|---|---|
| Average life span | 46 | 54 |
| Median life span | 75 | 100 |

EXAMPLE 5

Influence of L-Ala-L-Glu-L-Asp-Gly Tetrapeptide (SEQ ID NO: 11 on the Ageing Rate and Free Radical Processes in *Drosophila Melanogaster* of low Activity (LA) Strain Selected for a Low Sexual Activity of Males The impact produced by L-Ala-L-Glu-L-Asp-Gly tetrapeptide (SEQ ID NO: 1) on catalase activity, the content of the products of lipid peroxide oxidation (LPO), life span, and the ageing rate were studied in *Drosophila melanogaster* of LA strain.

One-day old flies were placed in test tubes, 10 individuals of the same sex in each. Every 2 days they were transferred to a fresh medium taking into consideration the number of deceased individuals. The average and maximal life spans were defined. The ageing rate was calculated by the parameters of Gomperz equation.

L-Ala-L-Glu-L-Asp-Gly tetrapeptide (SEQ ID NO: 1) was applied in the larvae of the $3^{rd}$ age in dose 0.00001% of the culture medium weight, which constituted approximately 0.015 mg/100 ml. Catalase activity was estimated by generally accepted methods in the homogenates of adult 14 days old flies. The experiment was carried out with a subsequent repetition.

Regression and dispersal analyses served as the basic technique of statistic processing. The authenticity of differences was confirmed by the method of minimal relevant diversity.

It was shown that L-Ala-L-Glu-L-Asp-Gly tetrapeptide (SEQ ID NO: 1) in females did not induce any alterations in the average life span, but did increase the maximal life span ($LS_{max}$). At the same time, the substance significantly extended the ALS in males. The analysis of the survival rate curves and Gomperz charts showed that L-Ala-L-Glu-L-Asp-Gly tetrapeptide (SEQ ID NO: 1) in females served as a geroprotector of the $1^{st}$ type (ALS and $LS_{max}$ were increased, though the ageing rate did not change in comparison with the control). In males, however, it acted as a geroprotector of the $3^{rd}$ type (ALS was increased, $LS_{max}$ did not change, in addition to which a tendency to an ageing rate increase was observed). At the same time, the analysis of survival rate in flies without taking into consideration their intersexual distinctions showed that $LS_{max}$ notably extended under the influence of L-Ala-L-Glu-L-Asp-Gly tetrapeptide (SEQ ID NO: 1).

The application of L-Ala-L-Glu-L-Asp-L-Gly tetrapeptide (SEQ ID NO: 1) in males significantly increased catalase activity, while in females the content of LPO products went down considerably. Suppression of intersexual distinctions confirmed a high anti-oxidation activity of L-Ala-L-Glu-L-Asp-Gly tetrapeptide (SEQ ID NO: 1).

TABLE 7

Influence of L-Ala-L-Glu-L-Asp-Gly tetrapeptide (SEQ ID NO: 1) on the life span parameters in female *Drosophila melanogaster* of LA strain

| Variant of the experiment | ALS (days) | Me (days) | $LS_{max}$ | $LnR_0$ (days$^{-1}$) | $G\ 10^2$ (days$^{-1}$) | MRDT |
|---|---|---|---|---|---|---|
| Control | 22 ± 1.0 | 28.5 | 36 ± 1.9 | −4.322 ± 0.4334 | 6.7 ± 1.78 | 3.4 |
| L-Ala-L-Glu-L-Asp-Gly Tetrapeptide (SEQ ID NO: 1) | 20 ± 1.3 | 17 | 44 ± 1.9* | −3.806 ± 0.2580 | 4.3 ± 0.90 | 3.8 |

Note:
$LS_{max}$ - maximal life span,
$LnR_0$ and $G\ 10^2$ - the parameters of Gomperz equation.
*$P < 0.05$ in comparison with the control indices.

TABLE 8

Influence of L-Ala-L-Glu-L-Asp-Gly tetrapeptide (SEQ ID NO: 1) on the life span parameters in male *Drosophila melanogaster* of LA strain

| Variant of the experiment | ALS (days) | Me (days) | $LS_{max}$ | $LnR_0$ (days$^1$) | $G\ 10^2$ (days$^{-1}$) | MRDT |
|---|---|---|---|---|---|---|
| Control | 19 ± 1.2 | 28.5 | 31 ± 0.9 | −4.579 ± 0.840 | 7.5 ± 4.62 | 3.3 |
| L-Ala-L-Glu-L-Asp-Gly Tetrapeptide (SEQ ID NO: 1) | 24 ± 0.96* | 28.5 | 33 ± 0.9 | −5.496 ± 0.711 | 10.9 ± 3.45 | 2.9 |

*$P < 0.01$ in comparison with the control indices.

Thus, the application of L-Ala-L-Glu-L-Asp-Gly tetrapeptide (SEQ ID NO: 1) in flies displayed the effect of ageing inhibition.

TABLE 9

Influence of L-Ala-L-Glu-L-Asp-Gly tetrapeptide (SEQ ID NO: 1) on the biochemical indices of free radical processes in *Drosophila melanogaster* of LA strain

| Variant of the experiment | Specific activity of catalase ($\mu$mole $H_2O_2$/mg of protein per min.) | Content of conjugated hydro-peroxides (nmole/g of tissue) |
|---|---|---|
| Control (females) | 43.31 | 1.469 |
| Control (males) | 49.27 | 1.247 |
| L-Ala-L-Glu-L-Asp-Gly tetrapeptide (SEQ ID NO: 1) (females) | 42.57 | 1.290* |
| L-Ala-L-Glu-L-Asp-Gly tetrapeptide (SEQ ID NO: 1) (males) | 57.44* | 1.202 |

*$P < 0.05$ in comparison with the control indices.

EXAMPLE 6

Influence of L-Ala-L-Glu-L-Asp-Gly Tetrapeptide (SEQ ID NO: 1) on the Ageing Rate and Free Radical Processes in *Drosophila Melanogaster* of the Environmental Adaptation (EA) Strain Selected for a Low Adaptability to the Environment

*Drosophila melanogaster* of EA strain served as a model for studying the influence of L-Ala-L-Glu-L-Asp-Gly tetrapeptide (SEQ ID NO: 1) on catalase activity, tissue chemoluminescence, and life span.

One-day old flies were placed in test tubes, 10 individuals of the same sex in each. Every 5 to 7 days they were transferred to a fresh medium, taking into account the number of deceased individuals. The average and maximal life spans were defined. The ageing rate was calculated by the parameters of Gomperz equation.

L-Ala-L-Glu-L-Asp-Gly tetrapeptide (SEQ ID NO: 1) was applied in the larvae of the $3^{rd}$ age in dose 0.00001% of the culture medium weight, which constituted approximately 0.015 mg/100 ml. Catalase activity and the intensity of chemoluminescence were estimated in the homogenates of adult 7-day old flies by generally accepted methods. The experiment was conducted with a subsequent 5 repetition.

Regression and dispersal analyses served as the basic technique of statistic processing. The authenticity of the differences was confirmed by the method of minimal relevant diversity.

The results of the investigation are displayed in Tables 10–13.

TABLE 10

Influence of L-Ala-L-Glu-L-Asp-Gly tetrapeptide (SEQ ID NO: 1) on the life span parameters in female *Drosophila melanogaster* of EA strain (Experiment 1)

| Variant | n | ALS (days) | $LS_{max}$ (days) | $LnR_0$ (days$^{-1}$) | $G\ 10^2$ (days$^{-1}$) |
|---|---|---|---|---|---|
| Control | 84 | 10.5 + 0.76 | 26 | −2.6 ± 0.18 | 7.7 ± 1.57 |
| L-Ala-L-Glu-L-Asp-Gly Tetrapeptide (SEQ ID NO: 1) | 72 | 16.4 ± 1.68** | 39 | −3.1 ± 0.21 | 3.6 ± 0.61* |

*$P < 0.05$ in comparison with the control indices;
**$P < 0.01$ in comparison with the control indices.

It is shown that L-Ala-L-Glu-L-Asp-Gly tetrapeptide (SEQ ID NO: 1) produces an effect on luminol-dependent chemoluminescence (Table 14). The reduction of this index indicates the activation of the anti-oxidation defence system in flies. The rise of intensity in the tissue anti-oxidation defence in this case is presumably associated with the activation of low-molecular endogenous anti-oxidants, such as glutathione, tocopherol, and the like.

Extension in the average and maximal life spans was observed only in cases of diminished viability and accelerated ageing in the control. As the displayed data show, it is the very case when the investigated tetrapeptide exerts a precise geroprotective effect.

TABLE 11

Influence of L-Ala-L-Glu-L-Asp-Gly tetrapeptide (SEQ ID NO: 1) on the life span parameters in male Drosophila melanogaster of EA strain (Experiment 1)

| Variant | n | ALS (days) | $LS_{max}$ (days) | $R_0$ (days$^{-1}$) | $G\ 10^2$ (days$^{-1}$) |
|---|---|---|---|---|---|
| Control | 80 | 14.2 ± 1.31 | 39 | −4.9 ± 0.44 | 9.2 ± 1.97 |
| L-Ala-L-Glu-L-Asp-Gly Tetrapeptide (SEQ ID NO: 1) | 100 | 10.8 ± 1.09 | 39 | −2.3 ± 0.26 | 3.3 ± 2.25 |

TABLE 12

Influence of L-Ala-L-Glu-L-Asp-Gly tetrapeptide (SEQ ID NO: 1) on the life span parameters in female Drosophila melanogaster of EA strain (Experiment 2)

| Variant | n | ALS (days) | $LS_{max}$ (days) | $R_0$ (days$^{-1}$) | $G\ 10^2$ (days$^{-1}$) |
|---|---|---|---|---|---|
| Control | 132 | 18.4 ± 0.62 | 41 | −4.7 ± 0.37 | 14.5 ± 2.26 |
| L-Ala-L-Glu-L-Asp-Gly tetrapeptide (SEQ ID NO: 1) | 115 | 16.7 ± 0.70 | 41 | −3.6 ± 0.41 | 4.2 ± 1.68 |

TABLE 13

Influence of L-Ala-L-Glu-L-Asp-Gly tetrapeptide (SEQ ID NO: 1) on the life span parameters in male Drosophila melanogaster of EA strain (Experiment 2)

| Variant | n | ALS (days) | $LS_{max}$ (days) | $R_0$ (days$^{-1}$) | $G\ 10^2$ (days$^{-1}$) |
|---|---|---|---|---|---|
| Control | 150 | 19.4 ± 1.20 | 45 | −4.2 ± 0.15 | 7.6 ± 0.58 |
| L-Ala-L-Glu-L-Asp-Gly Tetrapeptide (SEQ ID NO: 1) | 120 | 17.4 ± 0.88 | 45 | −3.0 ± 0.28 | 4.7 ± 0.94* |

*$P < 0.01$ in comparison with the control indices.

TABLE 14

Influence of L-Ala-L-Glu-L-Asp-Gly tetrapeptide (SEQ ID NO: 1) on the biochemical indices of free radical processes in Drosophila melanogaster of EA strain

| Variant of the experiment | Specific activity of catalase ($\mu$mole $H_2O_2$/mg of protein per min.) | Chemoluminescence intensity (conv. unit/ mg of protein per min.) |
|---|---|---|
| Control (females) | 83.65 ± 1.355 | 4.04 ± 0.135 |
| Control (males) | 102.10 ± 2.095 | 8.16 ± 0.090 |
| L-Ala-L-Glu-L-Asp-Gly tetrapeptide (SEQ ID NO: 1) (females) | 82.78 ± 2.957 | 4.61 ± 0.395 |
| L-Ala-L-Glu-L-Asp-Gly tetrapeptide (SEQ ID NO. 1) (males) | 100.39 ± 3.807 | 4.93 ± 0.109* |

*$P < 0.05$ in comparison with the control index.

EXAMPLE 7

Influence of L-Ala-L-Glu-L-Asp-Gly Tetrapeptide (SEQ ID NO: 1) on the Life Span of Drosophila Melanogaster of "Wild" Canton-S Strain In this research Drosophila melanogaster of "wild" Canton-S strain were employed.

L-Ala-L-Glu-L-Asp-Gly tetrapeptide (SEQ ID NO: 1) in the solution form was introduced into the culture medium provided for the growth of insects, which was cooled down to 50–60° C., with subsequent careful stirring and depositing it into test tubes.

To make the conditions of both the control and experimental population development identical, an amount of sodium chloride equal to that used for L-Ala-L-Glu-L-Asp-Gly tetrapeptide (SEQ ID NO: 1) solution was introduced into the culture medium for the control. The concentration of all the substances employed was calculated by the ratio to the mass of the culture medium provided for reproduction.

4-day old female flies underwent a randomly selected mating with males for 72 hours, one couple per each test tube, after which parental couples were removed from the test tubes. To form every new generation the posterity of 50 to 80 couples was used.

Life span (LS) was investigated on laboratory populations, each of them consisting of 90 individuals of each sex. Immediately after hatching the flies were randomly placed in test tubes, 10 individuals in each. Substitution of the culture medium was carried out 3 times a week.

Average values (ALS) and standard errors calculated by the traditional method were applied as life span distribution parameters. Average values were compared to each other with the application of Student t-criterion.

Table 15 displays the results of the life span distribution characteristics (average values and the standard errors of these average values) for all the experimental and control groups.

For experimental study 6 concentrations of L-Ala-L-Glu-L-Asp-Gly tetrapeptide (SEQ ID NO: 1) were selected: 0.01×, 0.1×, 1×, 5×, 7.5×, and 12.5×10$^{-6}$% of the culture medium weight.

L-Ala-L-Glu-L-Asp-Gly tetrapeptide (SEQ ID NO: 1) administered to males at the 4 lowest concentrations (0.01× to 5×10$^{-6}$%) exerted a significant geroprotective effect: ALS in the experimental groups showed a statistically relevant rise. Relative extension in the ALS of males was 3.3 to 10.8%.

In experiments conducted on females L-Ala-L-Glu-L-Asp-Gly tetrapeptide (SEQ ID NO: 1) exerted a geroprotective effect only in concentrations of 0.01× and $0.1 \times 10^{-6}\%$ with a significant increase in ALS correspondingly to 13.4% (P<0.004) and to 11.8% (P<0.03).

The efficacy of L-Ala-L-Glu-L-Asp-Gly tetrapeptide (SEQ ID NO: 1) applied in super-low concentrations, as shown by the obtained data, is unprecedented. It should be admitted that the application of L-Ala-L-Glu-L-Asp-Gly tetrapeptide (SEQ ID NO: 1) in *Drosophila melanogaster* did not alter the duration of their stage development, which, in general, reflected the lack of genotoxic effect produced by the studied substance.

animals. The animals of groups 2–5 underwent epiphysectomy (EE). In 3 weeks after the surgery (on the $21^{st}$ day) the animals of the $2^{nd}$ and $3^{rd}$ groups were subcutaneously injected with sodium chloride in dose 0.5 ml for the next 10 days. The animals of groups 4 and 5 were administered with L-Ala-L-Glu-L-Asp-Gly tetrapeptide (SEQ ID NO: 1) in dose 0.5 μg according to the same scheme.

Slaughtering of the animals and isolation of their organs were conducted from 10 a.m. to 12 noon by daylight with the use of Nembutal anaesthesia (50 mg/kg). The animals of groups 1, 2 and 4 were slaughtered in 3 days upon the final drug administration (on the $33^{rd}$ day after the operation and the onset of the experiment), while the animals of groups 3

TABLE 15

Influence of L-Ala-L-Glu-L-Asp-Gly tetrapeptide (SEQ ID NO: 1) on the life span parameters in *Drosophila melanogaster* of "wild" Canton-S strain

| No | Administered substance | Concentration $\times 10^{-6}\%$ | ALS ± statistic errors | Alterations in ALS % | t-Stud. P < |
|---|---|---|---|---|---|
| 1. Males | | | | | |
| 1. | Control | 0.01 | 32.55 ± 1.14 | +12.0 | 0.02 |
| 2. | L-Ala-L-Glu-L-Asp-Gly (SEQ ID NO: 1) | | 36.47 ± 1.09 | | |
| 3. | Control | 0.1 | 31.44 ± 1.35 | +10.8 | 0.05 |
| 4. | L-Ala-L-Glu-L-Asp-Gly (SEQ ID NO: 1) | | 34.85 ± 1.18 | | |
| 5. | Control | 1.0 | 32.45 ± 1.41 | | |
| 6. | L-Ala-L-Glu-L-Asp-Gly (SEQ ID NO: 1) | | 36.77 ± 1.44 | +13.3 | 0.04 |
| 7. | Control | 5.0 | 33.90 ± 1.14 | +11.3 | 0.02 |
| 8. | L-Ma-L-Glu-L-Asp-Gly | | 37.74 ± 1.16 | | |
| 9. | Control | 7.5 | 39.99 ± 0.97 | −0.03 | Statistically irrelevant |
| 10. | L-Ala-L-Glu-L-Asp-Gly (SEQ ID NO: 1) | | 39.98 ± 0.99 | | |
| 11. | Control | 12.5 | 37.32 ± 0.83 | −9.0 | 0.02 |
| 12. | L-Ala-L-Glu-L-Asp-Gly (SEQ ID NO: 1) | | 33.96 ± 1.01 | | |
| 2. Females | | | | | |
| 13. | Control | 0.01 | 31.22 ± 0.91 | +13.4 | 0.004 |
| 14. | L-Ala-L-Glu-L-Asp-Gly (SEQ ID NO: 1) | | 35.41 ± 1.07 | | |
| 15. | Control | 0.1 | 31.22 ± 0.91 | +11.8 | 0.03 |
| 16. | L-Ala-L-Glu-L-Asp-Gly (SEQ ID NO: 1) | | 35.41 ± 1.07 | | |
| 17. | Control | 1.0 | 36.17 ± 1.23 | −1.1 | Statistically irrelevant |
| 18. | L-Ala-L-Glu-L-Asp-Gly (SEQ ID NO: 1) | | 35.76 ± 1.35 | | |
| 19. | Control | 5.0 | 36.87 ± 1.40 | +3.2 | Statistically irrelevant |
| 20. | L-Ala-L-Glu-L-Asp-Gly (SEQ ID NO: 1) | | 38.04 ± 1.56 | | |
| 21. | Control | 7.5 | 33.74 ± 1.23 | −7.6 | Statistically irrelevant |
| 22. | L-Ala-L-Glu-L-Asp-Gly (SEQ ID NO: 1) | | 31.16 ± 1.21 | | |
| 23. | Control | 12.5 | 35.09 ± 1.36 | +5.6 | Statistically irrelevant |
| 24. | L-Ala-L-Glu-L-Asp-Gly (SEQ ID NO: 1) | | 37.06 ± 1.12 | | |

EXAMPLE 8

Influence of L-Ala-L-Glu-L-Asp-Gly Tetrapeptide (SEQ ID NO: 1) on the Extra-pineal Synthesis of Melatonin in Rats After Epiphysectomy The research was carried out on male Wistar rats weighing 130–140 g. The total number of the animals (23) was divided into 5 groups. The $1^{st}$ group (control) included intact and 5-in 12 days (on the $42^{nd}$ day after epiphysectomy). Examined were the main organs of the diffuse neuroendocrine system (DNES): stomach, thyroid gland, and pancreas.

The surgery—epiphysectomy—was conducted under ether anaesthesia according to the devised technique. A 1–1.5 cm long incision was made along the central line of the head. Upon the uncovering of the scull cap an aperture was drilled over the sinus confluence point by means of a hollow 0.5 cm-diameter auger, which was manufactured of a metal tube especially for the experiment. The epiphysis was extracted by means of ophthalmic forceps through the opening in the cranium. The trepanation aperture was covered with an osteal fragment. The skin incision was sewn with silk threads.

Fragments of the extracted organs were fixed for 24 hours in Buen sour liquid for optic microscopy and according to Karnovsky for electron microscopy. Material dehydration and filling it in with paraffin for optic microscopy, as well as epone mixture for ultra-structural examination were prepared according to generally accepted techniques. Paraffin sections (7 µm) were placed on a microscope slide covered with a poly-L-lysine film (Sigma). Ultra-thin sections (100 nm) prepared on LKB-7A microtome (LKB) were contrasted with uranyl acetate and plumbum citrate.

Histological and immunohistochemical examinations were carried out with a Jenamed-2 microscope (Zeiss). Electron-microscopic examination was conducted with a electronic JEM-100S microscope (JEOL).

For staining hematoxyline-eosin was applied. The total population of APUD-cytes in the pyloric and fundal stomach sections was determined according to Grimelius' histochemical silvering method (25).

Immunohistochemical exposure of enterochromophine-cells (EC-cells) was conducted by applying uniclonic antibodies of mice to serotonin (Dako, 1:15 titre). The uniclonic antibodies were identified according to avidin-biotin-peroxidase (ABP) method (Vectastain kit) in order to measure immune serum globulins of mice.

The quantitative studies were carried out by means of computer analysis system of microscopic imprints (Imstar) with the use of Morphostar and Colquant (Imstar) applied licensed computer programmes, in accordance with the basic principles of stereology and morphometry (26).

The quantitative density of enteroendocrine (END) ($N_{END}/1$ mm$^2$) and serotonin-positive cells ($N_{ser}/1$ mm$^2$) was estimated in 10 visual fields. The test area (S) constituted 5 mm$^2$.

For the statistical processing of the acquired data the non-parametric U-criterion by Mann/Whitney was applied.

Results of the DNES functional morphology studies conducted in epiphysectomised rats with L-Ala-L-Glu-L-Asp-Gly tetrapeptide (SEQ ID NO: 1) application showed that the tetrapeptide stimulated tissue and cellular metabolism.

It was shown that L-Ala-L-Glu-L-Asp-Gly tetrapeptide (SEQ ID NO: 1) administration exerted a compensatory effect upon the structural and functional organisation of DNES cells in animals exposed to epiphysectomy. Its effect was manifested within 3 days upon the end of the tetrapeptide administration through complete suppression of the epiphysectomy impact and maintained for 12 days, i.e. until the experiment termination with respect to all the examined organs.

The obtained data confirm that the main point of L-Ala-L-Glu-L-Asp-Gly tetrapeptide (SEQ ID NO: 1) application is the gastric EC-cells, in which L-Ala-L-Glu-L-Asp-Gly tetrapeptide (SEQ ID NO: 1) promotes the extra-pineal synthesis of serotonin and melatonin (Table 16), thus, in essence, providing a complete compensation for the extracted epiphysis.

So, results of the experimental investigation proved that L-Ala-L-Glu-L-Asp-Gly tetrapeptide (SEQ ID NO: 1) revealed no toxicity, normalised anti-oxidation defence indices, and regulated metabolic processes in the melatonin-producing structures of various tissues.

TABLE 16

Influence of L-Ala-L-Glu-L-Asp-Gly tetrapeptide (SEQ ID NO: 1) on the quantitative characteristics of the examined parameters in various stomach sections of epiphysectomised rats

| Group of animals | $N_{END}/1$ mm$^2$ Pyloric | $N_{END}/1$ mm$^2$ Fundal | $N_{ser}/1$ mm$^2$ Pyloric |
|---|---|---|---|
| Intact animals | 20 ± 1 | 48 ± 5 | 26 ± 2 |
| Control (epiphysectomised animals + sodium chloride solution) The 3$^{rd}$ day upon the end of drug administration | 30 ± 1* | 76 ± 1* | 32 ± 3* |
| Control (epiphysectomised animals + sodium chloride solution) The 12$^{th}$ day upon the end of drug administration | 15 ± 1* | 41 ± 4 | 19 ± 1* |
| Control (epiphysectomised animals + L-Ala-L-Glu-L-Asp-Gly (SEQ ID NO: 1)) The 3$^{rd}$ day upon the end of drug administration | 21 ± 1** | 64 ± 5** | 26 ± 2** |
| Control (epiphysectomised animals + L-Ma-L-Glu-L-Asp-Gly (SEQ ID NO: 1)) The 12$^{th}$ day upon the end of drug administration | 19 ± 1** | 47 ± 9 | 26 ± 3** |

*$P < 0.05$ in comparison with the indices for intact animals;
**$P < 0.05$ in comparison with the control indices.
Note: $N_{END}/1$ mm$^2$ - density of entero-endocrine cells; $N_{ser}/1$ mm$^2$ - density of serotonin-positive cells.

L-Ala-L-Glu-L-Asp-Gly tetrapeptide (SEQ ID NO: 1) properties revealed in the pre-clinical experiment show its manifested prophylactic and/or therapeutic application as a geroprotective substance.

Examples of the results received in the clinical trials of the proposed tetrapeptide demonstrate its pharmacological properties and confirm that the invention can be integrated with medical practice.

EXAMPLE 9

Efficacy of the Application of the Pharmacological Substance Containing L-Ala-L-Glu-L-Asp-Gly Tetrapeptide (SEQ ID NO: 1) in Patients With Disturbances of the Anti-oxidation Defence System for Premature Ageing Prevention The studied pharmacological substance was administered to 14 patients (34 to 69 years old) with age-related pathology (hypertension disease, ischemic heart disease, chronic gastritis, non-insulin-dependent diabetes mellitus) and reduction of the anti-oxidation defence indices in blood.

The substance containing L-Ala-L-Glu-L-Asp-Gly tetrapeptide (SEQ ID NO: 1) was administered intramuscularly in the form of an injection solution in a single daily dose of 10 µg per injection for 10 days.

In cases of the drug application a significant rise in superoxide dismutase activity and a decrease in the content of lipid peroxide oxidation products were observed (Table 17).

TABLE 17

Influence of L-Ala-L-Glu-L-Asp-Gly tetrapeptide (SEQ ID NO: 1) on blood anti-oxidation defence indices in age-related pathology

| Index | Before treatment | After treatment |
|---|---|---|
| Activity of superoxide dismutase, conv. unit/mg of protein | 0.26 | 0.61* |
| Products of spontaneous lipid peroxide oxidation, μM/l: | | |
| conjugated hydroperoxides; | 7.3 ± 0.6 | 2.5 ± 0.2* |
| Schiff bases | 4.6 ± 0.3 | 2.9 ± 0.2* |

*$P < 0.05$ in comparison with the pre-treatment indices.

Results of the therapy prove the restorative effect of the pharmacological substance containing L-Ala-L-Glu-L-Asp-Gly tetrapeptide (SEQ ID NO: 1) on the anti-oxidation defence system of the organism.

EXAMPLE 10

Efficacy of the Pharmacological Substance Containing L-Ala-L-Glu-L-Asp-Gly Tetrapeptide (SEQ ID NO: 1) Applied for Premature Ageing Prevention in Patients With Disturbances of Melatonin Synthesis The pharmacological substance was administered to 11 patients at the age of 39 to 63 years old suffering aspirin bronchial asthma. The main characteristic of this disease consists in association of asphyxia fits with intolerance to acetylsalicylic acid and other non-steroid anti-inflammatory substances. N-acetyl-5-methoxykynurenamine (N-AMK), an analogue of acetylsalicylic acid in its chemical structure, is known to be formed in the organism through the metabolism of melatonin, an epiphyseal hormone. Melatonin synthesis and, consequently, the level of endogenous N-AMK are significantly decreased in patients with aspirin bronchial asthma, which is confirmed by the low excretion in urine of 6-sulfatoxymelatonin, the basic melatonin metabolite.

This substantiated a new pathogenetic approach to the treatment for aspirin bronchial asthma by means of correcting melatonin level in the organism with the pharmacological substance containing L-Ala-L-Glu-L-Asp-Gly tetrapeptide (SEQ ID NO: 1).

The substance was administered intramuscularly in the form of an injection solution daily in the morning in a dose of 10 μg for 10 days.

The patients were treated during the phase of fading exacerbation or disease remission against accompanied by permanent anti-asthma therapy, which included inhalation and oral glucocorticoids.

Prior to, during the treatment, and later on monthly the patients subjectively estimated their health state by such symptoms as coughing, sputum discharge, hard breathing, breast stuffing, whistling rale, fits of asphyxia, intolerance to physical loads, cold, and smells. Clinical effect produced by the preparation was estimated immediately after the treatment and within the next 7 months on the basis of analyses reported by the patients, which included the data on their health state dynamics, capacity for work, psychological condition, sleep impairments, and daily doses of the anti-asthmatic drugs taken.

Before the onset of the treatment and right after the administration of the final dose of the drug external respiration function was estimated in all the patients with reference to the following parameters: vital breathing capacity (VBC), tidal volume (TV), total lung capacity (TLC), forced vital breathing capacity (FVBC), maximum volumetric exhalation rate (MVexhR), maximum volumetric exhalation rate by 50% and 75% forced VBC ($VBC_{50}$ and $VBC_{75}$), forced exhalation volume per second ($FEV_1$). These parameters were measured as a per cent of the initial values. Additionally, the specific conduction of the bronchial tree in cm of aquatic column was measured. The whole complex of tests was repeated within 15 min after an inhalation with Berotek. Dynamics of MVR, $VBC_{50}$, and $VBC_{75}$ after a Berotek inhalation was estimated as a per cent of the initial values. The FEV index in all the patients before treatment was less than 80% of the due value.

Content of 6-sulfatoxymelatonin, the basic melatonin metabolite, was measured before, immediately after, and within 10 days after the treatment in the urine taken in the daytime (from 9 a.m. to 21 p.m.) and at night (from 21 p.m. to 9 a.m.), according to the immunofermental method by means of "DRG Instrument GmbH" kits (Marburg, Germany).

Results of the investigations confirmed that improvement in clinical state by the end of the treatment was observed in the overwhelming majority of patients treated with the studied pharmacological substance. A reduced frequency of day asthma symptoms, decreased intolerance to physical work, strong smells, and cold air, as well as sleep recovery were registered. Objective examination of the patients revealed a decrease in or an absolute disappearance of whistling rale in the lungs—the symptoms of bronchial obstruction. Examination of the external respiratory function immediately after the treatment termination did not reveal any essential alterations in VBC, MVexhR, $FEV_1$, TV/TLC. However, the patients, exposed to the tetrapeptide-containing pharmacological substance, showed an improvement in the reaction to Berotek on the level of distal bronchi. Excretion of 6-sulfatoxymelatonin in urine increased, indicating an increase in melatonin production not only at night, but also in the daytime.

References

1. Harman D. Ageing and disease: extending functional life span//Ann. N.Y. Acad. Sci.-1996.-Vol. 786.-P. 321–336.
2. Pierpaoli W. Neuroimmunomodulation of ageing: a program in the pineal gland//Ann. N.Y. Acad. Sci.-1998.-Vol. 840.-P. 491–497.
3. Yu B. P., Yang R. Critical evaluation of the free radical theory of ageing: a proposal for the oxidative stress hypothesis//Ann. N. Y. Acad. Sci.-1996.-Vol. 786.-P. 1–11.
4. Harman D. Free radical theory of ageing: effect of free radical reaction inhibitors on the mortality rate of male $LAF_1$ mice//J. Gerontol.-1968.-Vol. 23.-P. 476.
5. Mashkovsky M. D. Pharmaceutical substances. (Doctors textbook).-Moscow: Medicine, 1993.-Part. 11, Ch. 10.-P. 213–215.
6. Comfort A., Youhotsky-Gore J., Pathmanathan K. Effect of ethoxyquin on the longevity of C3H mice //Nature.-1971.-Vol. 229.-P. 254–255.
7. Obukhova L. K. Chemical geroprotectors, increase in the life span//Uspekhi Khimii.-1975.-Vol. 44.-P. 1914–1925.
8. Emanuel N. M., Obukhova L. K., Smirnov L. D., Bounto T. V. Inhibition of ageing processes in laboratory mice by administration of chlorhydrate 2-ethyl-6-methyl-3-oxypyridine//Izvestiya of the USSR Acad. of Sciences, Series on Biology.-1977.-K2 1.-P. 32–37.
9. Obukhova L. K., Emanuel N. M. Molecular mechanisms of ageing inhibition by means of anti-oxidants//General Problems in Biology / All-Union Institute of Research and Technical Information.-1984.-Vol. 4.- P. 44–80.

10. Frolkis V. V., Mouradjan Kh. K. Experimental ways to prolong life span.-Leningrad: Nauka, 1988.
11. Baker G. T. Effect of various antioxidants on ageing in Drosophila//Toxicol. Ind. Health.-1993.-Vol. 9.- P. 163–186.
12. Epstein J., Himmelhoch S., Gershon D. Studies on ageing in nematodes. III. Electron-microscopical studies on age-associated cellular damage//Mech. Age. Dev.-1972.-P. 245–255.
13. Massie H. R., Aiello V. R., Williams T. R. et al. Effect of vitamin A on longevity//Exp. Gerontol.-1993.-Vol. 28.-P.601–610.
14. Kumari M. V., Yoneda T., Hiramatsu M. Effect of "beta CATECHIN" on the life span of senescence accelerated mice (SAM-P8 strain)//Biochem. Mol. Biol. Int.-1997.-Vol. 41, N 5.-P. 1005–1011.
15. Boldyrev A. A., Karnozin. Significance of biology and ways of applying it to medicine.-Moscow: Publ. Moscow State University, 1998.-320 p.
16. Pierpaoli W., Regelson W. Pineal control of ageing: effect of melatonin and pineal grafting in ageing mice// Proc. Nat. Acad. Sci. USA—1986.-Vol. 91.-P. 787–791.
17. Reiter R., Tang L., Garcia J. J., Mucoz H. A. Pharmacological actions of melatonin in oxygen radical pathophysiology//Life Sci.-1997.-Vol. 60, N 25.-P. 2255–2271.
18. Mashkovsky M. D. Pharmaceutical substances. (Doctors textbook).-Moscow: Medicine, 1993.-Part. I, Ch. 3.-P. 375.
19. Jakubke Kh. -D., Eshkeit Kh. Amino acids, peptides, proteins: transl. from German—Moscow: Mir, 1985.-456p.
20. Mylnikov S. V., Smirnova A. D. Mortality rate dynamics in inbred selected strains and their hybrids in *Drosophila melanogaster*.//Ontogenesis.-1994.-Vol. 25, N 4.-P. 7–11.
21. Agostini A., Gerli G. C., Beretta L., Bianchi M. Superoxide dismutase, catalase and glutathione peroxidase activities in maternal and cord blood erythrocytes//J. Clin. Chem. Clin. Biochem.-1980.-Vol. 18.-P. 771–773.
22. Kricka L. S., Thorpe G. H. The intensity of free radical oxidation//Chemoluminescent and bioluminescent methods in analytical chemistry.-1983.-Vol.108.-P.1274–1296.
23. Orr W. C., Sohal R. S. Extension of life span by overexpression of superoxide dismutase and catalase in *Drosophila melanogaster*//Science.-1994.-Vol.263.-P.1128–1130.
24. Urbach V. Ju. Mathematical statistics for biologists and physicians.-Moscow, 1963.
25. Kvetnoy I. M., Juzhakov V. V. Staining of endocrine gland tissue and APUD-system elements.//Microscopic Techniques: Manual.//Eds.: D. S. Sarkisov, Ju. L. Perov-Moscow: Medicine, 1996.-P.375-418.
26. Avtandilov G. G. Medical morphometry: Manual.-Moscow: Medicine, 1990.-384 p.

What is claimed is:

1. Tetrapeptide L-alanyl-L-glutamyl-L-aspartyl-glycine (SEQ ID NO: 1) of the general formula L-Ala-L-Glu-L-Asp-Gly (SEQ ID NO: 1).

2. A pharmacological substance, containing an active base and a pharmacologically admissible carrier, wherein said active base comprises an effective amount of L-Ala-L-Glu-L-Asp-Gly (SEQ ID NO: 1) tetrapeptide or its salts.

3. The substance described in claim 2, wherein said salts are salts of amino groups and are selected from the group consisting of acetate, hydrochloride, and oxalate.

4. The substance described in claim 2, wherein said salts are salts of carboxyl groups, selected from the group consisting of sodium, potassium, calcium, lithium, zinc, and magnesium.

5. The substance described in claim 2, wherein said substance is presented in a form suitable for parenteral administration.

6. The substance described in claim 2, wherein said substance is presented in a form suitable for intranasal administration.

7. The substance described in claim 2, wherein said substance is presented in a form suitable for oral administration.

8. The substance described in claim 2, wherein said substance is presented in a form suitable for local application.

9. A method of treating symptoms of premature ageing in a patient in need thereof comprising the step of administering to said patient a pharmacological substance comprising L-Ala-L-Glu-L-Asp-Gly tetrapeptide (SEQ ID NO: 1) or its salts in an amount sufficient to prevent said symptoms of premature ageing.

10. A method for increasing superoxide dismutase activity in a subject in need thereof, comprising the step of
   administering to said subject an amount of the tetrapeptide L-Ala-L-Glu-L-Asp-Gly (SEQ ID NO: 1) or its salts sufficient to cause an increase in superoxide dismutase activity in said subject.

11. A method for decreasing lipid peroxide oxidation products in a subject in need thereof, comprising the step of
   administering to said subject an amount of the tetrapeptide L-Ala-L-Glu-L-Asp-Gly (SEQ ID NO: 1) or its salts sufficient to decrease lipid peroxide oxidation products in said subject.

12. A method for reducing asthma symptoms in a patient in need thereof, comprising the step of
   administering to said patient an amount of the tetrapeptide L-Ala-L-Glu-L-Asp-Gly (SEQ ID NO: 1) or its salts sufficient to reduce asthma symptoms in said subject.

13. A method for increasing melatonin production in a subject in need thereof, comprising the step of
   administering to said subject an amount of the tetrapeptide L-Ala-L-Glu-L-Asp-Gly (SEQ ID NO: 1) or its salts sufficient to increase melatonin production in said subject.

14. The substance described in claim 2 wherein said salts are selected from the group consisting of salts of organic cations and salts of inorganic cations.

15. The substance described in claim 2 wherein said salts are selected from the group consisting of ammonium and triethylammonium.

16. The method of claim 9 wherein said symptoms are selected from the group consisting of a decrease in superoxide dismutase activity, an increase in lipid peroxide oxidation products and a decrease in melatonin production.

17. The method of claim 9 wherein said salts are salts of amino groups and are selected from the group consisting of the salts of acetate, hydrochloride, and oxalate.

18. The method of claim 9 wherein said salts are salts of carboxyl groups and are selected from the group consisting of the salts of sodium, potassium, calcium, lithium, zinc, and magnesium.

19. The method of claim 9 wherein said salts are selected from the group consisting of salts of organic cations and salts of inorganic cations.

20. The method of claim 9 wherein said salts are selected from the group consisting of ammonium and triethylammonium.

* * * * *

UNITED STATES PATENT AND TRADEMARK OFFICE
CERTIFICATE OF CORRECTION

PATENT NO. : 6,727,227 B1
DATED : April 27, 2004
INVENTOR(S) : Khavinson

It is certified that error appears in the above-identified patent and that said Letters Patent is hereby corrected as shown below:

Title page,
Item [54], Title, please substitute "TETRAPETIDE REVEALING" with
-- TETRAPEPTIDE REVEALING --.
Item [73], Assignee, please substitute "Obschestvo S Ogranichennoi Otvetstven-Nostiju "Klinika Instituta Bioregulyatsii Gerontologii"" with -- Obschestvo S Ogranichennoi Otvetstvennostiju "Klinika Instituta Bioregulyatsii I Gerontologii" --.

Signed and Sealed this

Sixteenth Day of August, 2005

JON W. DUDAS
*Director of the United States Patent and Trademark Office*